United States Patent
Geffard (10) Patent No.: US 10,596,271 B2
(45) Date of Patent: Mar. 24, 2020

(54) USE OF PLL FOR IMPROVING THE STABILITY OF MOLECULES IN SOLUTION

(71) Applicant: HYDRO-FILL, Cenon (FR)

(72) Inventor: Michel Geffard, Talence (FR)

(73) Assignee: HYDRO-FILL, Cenon (FR)

( * ) Notice: Subject to any disclaimer, the term of this patent is extended or adjusted under 35 U.S.C. 154(b) by 0 days.

(21) Appl. No.: 15/536,840

(22) PCT Filed: Dec. 17, 2015

(86) PCT No.: PCT/FR2015/053568
§ 371 (c)(1),
(2) Date: Aug. 3, 2017

(87) PCT Pub. No.: WO2016/097618
PCT Pub. Date: Jun. 23, 2016

(65) Prior Publication Data
US 2018/0008722 A1     Jan. 11, 2018

(30) Foreign Application Priority Data

Dec. 17, 2014  (FR) .................................. 14 62595

(51) Int. Cl.
| A61K 47/34 | (2017.01) |
| A61K 47/64 | (2017.01) |
| A61K 47/54 | (2017.01) |
| A61K 47/69 | (2017.01) |
| A61K 38/37 | (2006.01) |
| A61K 38/38 | (2006.01) |
| A61K 38/42 | (2006.01) |
| A61K 39/395 | (2006.01) |
| C07K 16/44 | (2006.01) |

(52) U.S. Cl.
CPC .......... *A61K 47/6455* (2017.08); *A61K 38/37* (2013.01); *A61K 38/385* (2013.01); *A61K 38/42* (2013.01); *A61K 39/39583* (2013.01); *A61K 39/39591* (2013.01); *A61K 47/34* (2013.01); *A61K 47/542* (2017.08); *A61K 47/645* (2017.08); *A61K 47/6905* (2017.08); *C07K 16/44* (2013.01)

(58) Field of Classification Search
CPC ............................ A61K 47/34; A61K 47/6455
See application file for complete search history.

(56) References Cited

U.S. PATENT DOCUMENTS

| 5,554,748 A * | 9/1996 | Sieving | A61K 49/085 540/465 |
| 6,114,388 A * | 9/2000 | Geffard | A61K 47/645 514/1.3 |
| 8,398,997 B2 * | 3/2013 | Dake | A61K 8/64 424/247.1 |

FOREIGN PATENT DOCUMENTS

| WO | WO-9615810 A1 * | 5/1996 | ........... A61K 47/645 |
| WO | WO-2005084361 A2 * | 9/2005 | ........... A61K 9/0014 |

OTHER PUBLICATIONS

Shen et al. Conjugation of Poly-L-Lysine to Albumin and Horseradish Peroxidase . . . Proceedings of the National Academy of Sciences, US. Apr. 1, 1978, vol. 75, No. 4, pp. 1872-1876. (Year: 1978).*
Mislick et al. Transfection of Folate-Polylysine DNA Complexes: Evidence for Lysosomal Delivery. Bioconjugate Chemistry. 1995, vol. 6, No. 5, pp. 512-515. (Year: 1995).*
Zhou et al. Lipophilic polylysines mediate efficient DNA transfection in mammalian cells. Biochimica et Biophysica Acta—Biomembranes. 1991, vol. 1065, pp. 8-14. (Year: 1991).*
Ginobbi et al. Folic Acid-Polylysine Carrier Improves Efficacy of c-myc Antisense Oligodeoxynucleotides on Human Melanoma (M14) Cells. Anticancer Research. 1997, vol. 17, pp. 29-36 (Year: 1997).*
Erica Ollmann Saphire, et al., Crystal Structure of a Neutralizing Human IgG against HIV-1: A Template for Vaccine Design, Science: New Series, Aug. 10, 2001, pp. 1155-1159, vol. 293, No. 5532.
Jacky Chi Ki Ngo, et al., Crystal Structure of Human Factor VIII: Implications for the Formation of the Factor IXa-Factor VIIIa Complex, Structure, Apr. 2008, pp. 597-606, vol. 16, Elsevier Ltd.
Arturo Mangas, et al., Antisera and immunocytochemical techniques, Brain Molecules: From Vitamins to Molecules for Axonal Guidance, 2008, pp. 1-25.
Ananyo A. Bhattacharya, et al., Binding of the General Anesthetics Propofol and Halothane to Human Serum Albumin, The Journal of Biological Chemistry, Dec. 8, 2000, pp. 38731-38738, vol. 275, No. 49.
M.K. Safo, et al., The Enigma of the Liganded Hemoglobin End State: A Novel Quaternary Structure of Human Carbonmonoxy Hemoglobin, Biochemistry, 2005, pp. 8347-8359, vol. 44.

(Continued)

*Primary Examiner* — Jeffrey E. Russel
(74) *Attorney, Agent, or Firm* — Young & Thompson (57) ABSTRACT

The invention relates to a molecular complex comprising at least one polylysine conjugate (PLL), comprising a main PLL straight chain and at least one molecule F having an average molecular weight of between 50 daltons and 1000 daltons that is covalently bonded to said main chain, and at least one molecule M that is unstable in solution, the conjugate(s) and the molecule(s) M being bonded by means of a non-covalent bond. The invention also relates to a composition comprising a complex of this kind, to a method for obtaining said composition and use thereof, and to the use of one or more PLL-based conjugates for improving the hydrophilicity, the effectiveness, and the activity of a molecule that is unstable in solution, over a time period that is compatible with the use of said molecule. The invention also relates to a method for identifying a PLL-based conjugate or a combination of a plurality of PLL-based conjugates that makes it possible to improve the hydrophilicity, the effectiveness, and the activity of a molecule that is unstable in solution, and to a kit for implementing said method.

10 Claims, 4 Drawing Sheets

(56) References Cited

OTHER PUBLICATIONS

Michel Geffard, et al., First demonstration of highly specific and sensitive antibodies against dopamine, Brain Research, 1984, pp. 161-165, vol. 294, Elsevier Science Publishers B.V.
Michel Geffard, et al., Neurobiologie, C.R. Acad. Sc. Paris, t. 295, Dec. 20, 1982, pp. 797-802, Series III.
Shouming Wang, et al., Studies of Benzothiophene Template as Potent Factor IXa (FIXa) Inhibitors in Thrombosis, Journal of Medicinal Chemistry, 2010, pp. 1465-1472, vol. 53.

* cited by examiner

USE OF PLL FOR IMPROVING THE STABILITY OF MOLECULES IN SOLUTION

This invention has as its object a particular molecular complex that comprises a polylysine (PLL)-based conjugate and a molecule that is unstable in solution. Its object is also a composition that comprises such a complex, a production method, and its use.

The invention also has as its object the use of one or more PLL-based conjugates for improving the hydrophilicity and the effectiveness/activity of a molecule that is unstable in solution over a period of time that is compatible with the use of said molecule.

This invention also relates to a method for identifying a conjugate or a combination of multiple PLL-based conjugates making it possible to improve the hydrophilicity and the effectiveness/activity of a molecule that is unstable in solution as well as a kit for its implementation.

A large number of macromolecules of general interest, in particular in the pharmaceutical, cosmetic, nutritional, or diagnostic field, are unstable in solution, not very soluble, or insoluble. They lose, partially or totally, their activity in solution and therefore become difficult to use or even totally unusable whereas they have an activity that is pharmacological, cosmetic, nutritional, and/or diagnostic.

The reasons for such instability in solution are diverse but generally result in the inability of the molecule to maintain a balance between different stabilizing interactions and its structural entropy that tends to destabilize the whole.

This instability has significant repercussions in particular for the industrialist who has invested means in a research and development program resulting in this unusable molecule, but also for the individuals deprived of its beneficial effects.

The technical solutions that are currently known for remedying this phenomenon of instability are often very cumbersome, require a considerable amount of development time and are also not very suitable for therapeutic, cosmetic, or nutritional use or as a diagnostic reagent of the molecule.

For example, the unstable solutions of molecules for pharmaceutical purposes are generally preserved at temperatures approaching −80° C. They must be reheated and administered to a patient undergoing treatment. This also presents a major drawback linked to energy expenditures necessary to maintaining a stabilization temperature of −80° C., a logistical problem linked to the necessary synchronization between the steps for reheating the solution by being careful to avoid the precipitation of the molecule, thus the uncertainty as to the actual quantity of the administered active molecule, and the route of administration for the pharmaceutical products.

Furthermore, methods for stabilization of macromolecules are already known, such as micro-encapsulation, the formation of nanoparticles, or else the vectorization, but these methods are no longer satisfactory.

The micro-encapsulation is a method by which a product—solid, liquid, or pasty—is incorporated in microparticles. In the health field, microparticles are used so as to carry out a deposition of a quantity of medication that is slowly released into the body. This system, although effective in certain cases for stabilizing and releasing a molecule of interest in vivo, is incapable of stabilizing it in liquid solution ex vivo if the former is unstable in solution. In addition, the polymers that are used in general for the formation of these microcapsules are derivatives of lactic and glycolic acids (PLGA, PLA), ethyl cellulose, or poly-epsilon-caprolactone, which are biodegradable and likely to leave "pollutant traces" for the recipient and the environment.

Nanoparticles are used in biomedical research and in medicine. The nanoparticles are ultrafine particles of which one of the three dimensions is less than 100 nm. This technology, in addition to its generally prohibitive cost, has a certain number of limitations and drawbacks. Actually, the synthesis of these products should be fully reproducible; their physico-chemical properties should be studied in depth and with great precision; the surface of the nanoparticles should most often be covered by molecules or polymers that make it possible to increase its colloidal stability and biocompatibility. Finally, the mechanisms of degradation of the nanoparticles should also be studied in an in-depth manner, and the risks of cellular, physiological, and histological toxicity should be seriously evaluated. The use of nanotechnology therefore involves significant physical risks that can be both environmental risks and risks to the health of individuals who use them but also individuals who handle the nanoparticles during their production. Other drawbacks are linked to the fact that exposure to nanoparticles should be minimal and/or monitored by a traceability that should make it possible to know at any time where the nanoparticles are located, in what product, in what packaging.

Thus, the known methods, although making it possible in a certain proportion to "stabilize" an "in-vivo" macromolecule, i.e., in particular to increase its bioavailability and its stability relative to its degradation by enzymes and other proteins such as proteases, lipases, and glucosidases, for example, are incapable of stabilizing an "ex-vivo" macromolecule, i.e., in particular:

on the one hand, to maintain the macromolecule in solution (without it precipitating) in the liquid phase, for example for a primarily aqueous solution, at a temperature that is higher than approximately 0° C. for a fairly long period (which can range up to several months or years) to make possible an easy handling of the macromolecule in solution and its storage in the solid phase (in frozen form) but also in the liquid phase (for example at ambient temperature), and, on the other hand, also to maintain its activity in the solid phase and in the liquid phase, at a temperature that is higher than 0° C., for the entire period of its storage (which can range up to several months or years).

In general, a macromolecule of interest formulated with any one of the methods of the state of the art is stable in ex-vivo liquid solution only for a very short time, from several seconds to several minutes, and even several hours.

There is therefore a significant need for an alternative system that makes it possible not only to retain the advantages of a good vectorization of the in-vivo macromolecule, but also the stabilization of the ex-vivo macromolecule in liquid solution so as to improve its storage and its handling.

There is also an equally significant need for a system that remedies at least one of the above-cited drawbacks in reference to the systems that are already known, in particular a system:

making possible the stabilization in a solution of a molecule that is unstable in solution, preferably at a temperature where the solution is in the liquid phase and for a fairly long period to make possible the handling and/or the storage of the macromolecule, making it possible to maintain the activity, in particular the biological activity, of a molecule that is unstable in solution even in the complexed form, making it possible to maintain the activity in solution, in particular the biological activity, of a molecule that is unstable in solution preferably at a temperature where the solution is in the liquid phase and for a fairly long period to make possible the handling and/or the storage of the macromolecule, not having an immunogenic nature, easy to use, inexpensive to use, making it possible to protect the molecule that is unstable in solution from the chemical, biochemical, enzymatic or immunological inactivation that the molecule is likely to undergo, making it possible to improve the pharmacokinetics and in particular making possible a controlled release of the molecule that is unstable in solution, and therefore to keep its concentration within the zone of therapeutic effectiveness, not toxic or not very toxic to the environment, making possible the reduction of undesirable side effects of the molecule preventing phenomena of metabolism, elimination, or toxicity, making it possible to reduce the toxic effects, while ensuring the delivery of a sufficient quantity of the molecule in the active site, making possible a selective and specific release of the macromolecule, by means of ligands that can interact with target cells, making it possible to maintain the pharmacological, cosmetic, or nutraceutical activity or the like of the molecule when it is used.

To respond to this, the object of this invention is a non-covalent molecular complex that comprises at least one conjugate, preferably a mono-functional conjugate, of a PLL. The use of such a conjugate with a molecule that is unstable in solution makes it possible to improve the solubility of the molecule, its stability, and to extend and/or maintain the activity of the molecule in solution.

The PLL conjugates are known in particular for their use in the pharmaceutical field. The international patent application WO96/15810 in particular discloses the use of these conjugates for the preparation of pharmaceutical compositions that are useful in the treatment of neuronal degenerescence, autoimmunity, and malignant cell proliferation.

Nevertheless, these conjugates have never been used to form molecular complexes via non-covalent bonds with molecules that are unstable in solution to improve their stability in solution and to extend or maintain their activity.

The object of the invention is to target a molecular complex that comprises:
 at least one PLL conjugate, comprising:
  a main PLL straight chain, and
  at least one molecule F that has a molecular weight of between 50 dalton and 1000 dalton and is linked covalently to said main chain,
 at least one molecule M that is unstable in solution,
with the conjugate(s) and the molecule(s) M being linked/interacting by a non-covalent bond.

The invention also has as its object a method for obtaining such a complex, compositions that contain it, and its use.

The object of the invention is also the use of at least one PLL conjugate, comprising:
 a main PLL straight chain, and
 at least one molecule F that has a molecular weight of between 50 dalton and 1000 dalton and is linked covalently to said main chain, in a hydrophilic solution, to improve the stability in solution of a molecule M that is unstable in solution, by forming a molecular complex with this molecule M by a non-covalent bond. The invention also has as its object a kit for implementing this use.

Finally, the invention also relates to a method for identification of at least one PLL conjugate that can be linked in a non-covalent way to a given molecule M that is unstable in solution, as well as a kit for implementing this method.

In a general way, the invention makes it possible to stabilize in solution a molecule M in the form of a molecular complex. Actually, in an unexpected and surprising way, the invention makes it possible to provide a second "life" to numerous molecules that are unstable in solution, in particular macromolecules, in particular macromolecules of therapeutic advantage that have been abandoned or have not been used commensurate with their value, by combining said molecule with one or more selected PLL-based conjugate(s) depending on the molecule under study.

Against all expectations, it was shown that the molecules that were unstable in solution, in general in solution with a hydrophilic and primarily aqueous nature, can, owing to the presence of certain PLL conjugates, be stored/maintained in liquid solution, i.e., for example, at a temperature of higher than 0° C. for the primarily aqueous solutions, and even at ambient temperature, for several days, months and even probably years, without a significant loss in their initial pharmacological activity or one or the other of their properties.

In an equally surprising manner, the complexes of the invention that are thus formed and stable ex vivo can also be directly used in vivo in therapeutic, cosmetic, nutritional, surgical or diagnostic applications, and can in particular be administered to a patient without there being any particular problems linked to the toxicity. In these terms, the complexes of the invention can also act as therapeutic vectors, protecting in vivo the molecule M that is complexed against the attacks, in particular, on the metabolic, enzymatic and immune systems of the animal or human body.

Other advantages and characteristics of the invention will emerge from the following detailed description, given with regard to non-limiting examples and accompanying figures in which.

DEFINITIONS

In terms of this invention, "complex" or "molecular complex" is defined as an entity formed by bringing into contact a molecule M that is unstable in solution and one or more PLL conjugate(s) linked by a non-covalent bond.

In terms of the invention, "PLL conjugate" is defined as a molecule that is obtained from a covalent coupling to a PLL of one or more molecules F. "Monofunctional PLL conjugate" is defined as the product of coupling a molecule F to the PLL. "Polyfunctional PLL conjugate" is defined as the product of coupling at least two molecules F. For example, a bifunctional conjugate can be shown by the formula: molecule F1-PLL-molecule F2. In terms of the invention, "molecule F" is defined as a substituent or a molecule that is non-immunogenic.

"Substituent" is defined as a molecule of low molecular weight that is in general between approximately 50 dalton and approximately 1000 dalton, preferably between approximately 200 dalton and approximately 600 dalton, and more preferably between approximately 150 dalton and approximately 500 dalton, which can be linked by a covalent bond or can interact by a covalent bond with a PLL in epsilon (ε)-amine position of the carbon chain.

"Immunogenic" is defined as any molecule that can induce an immune reaction. A "non-immunogenic" molecule is therefore a molecule that does not induce an immune reaction.

In terms of this invention, "PLL" or "polylysine" is defined as a polypeptide or homopolymer that consists primarily of straight L or D-lysine (i.e., not branched by one or more other lysines) or primarily straight L-lysine. It corresponds to the formula:

(cf. *Merck Index*, 10$^{th}$ Edition, Abstract No. 7444).

In terms of the invention, "molecule M that is unstable in solution" is defined as a molecule that is unstable in solution, preferably a macromolecule. It may be in particular a protein, a lipid, a sugar, a nucleic acid, or any other biomolecule of large size; "unstable in solution" is defined as a molecule that has a reduction or a loss of activity when it is put into solution in a solvent, in particular in an aqueous solvent. It may involve hydrophobic or slightly hydrophilic molecules, or hydrophilic molecules, but whose activity is reduced in solution.

In terms of this description, a "non-covalent" bond is defined as any bond that is not covalent, in particular a bond of the ionic, hydrogen, or van der Waals type.

In terms of the invention, "pharmacological or biological activity" is defined as the observed consequence that the absorption of a molecule or a substance by a body can have as obtained by an analysis method making it possible to detect such an activity. The former can be evaluated, for example, by observing and evaluating the selective occupation of a recipient or the specific interaction with an enzyme or protein (e.g., the antigen-antibody interaction) of the molecule or substance of interest. Within the framework of this application, the reduction or the loss of the pharmacological activity of a substance or macromolecule of interest in a liquid solution is an indication of the instability of said substance in liquid solution.

In terms of this invention, "initial biological activity" or "initial pharmacological activity" is defined as the biological or pharmaceutical activity of a complex according to the invention as measured for the first time after its solubilization. The time that has elapsed between the solubilization of the complex and the first measurement of activity can be variable and subject to the influence of various parameters, including in particular the rapidity of execution of the taking of measurements, whether it is automated or manual. To improve the reproducibility of the experiment, it will be possible to standardize taking the first measurement that can be carried out, for example, approximately at least 3 minutes, preferably approximately 15 minutes, after the solubilization of the complex according to the invention. "Original biological activity" or "original pharmacological activity" is defined as the biological or pharmacological activity of a molecule before it is brought into contact (i.e., its complexing) with one or more conjugates as defined in this application. "Variation of the pharmacological or biological activity" is defined as the absolute value of the difference between the observed and measured value of the initial activity and the observed and measured value of the activity at a moment "t" after the solubilization of the macromolecule. "Maintaining the pharmacological or biological activity" is defined as a variation of the pharmacological or biological activity as defined above of at most 30%, preferably at most 20%, preferably at most 10%, more preferably of at most 5%, or else at most 1%.

In terms of this invention, "aqueous solvent" is defined as a solvent that is primarily or essentially aqueous, i.e., containing at least approximately 70% water, preferably at least approximately 80% water, and more preferably at least approximately 90% water or else at least approximately 95% water.

In terms of the invention, "solution in the liquid phase" or "solution in the liquid state" is defined as a solution that has not reached its freezing point. By way of example, an aqueous or primarily aqueous solution kept at a temperature that is lower than approximately 0° C., preferably lower than approximately −5° C., cannot be considered as being in the liquid phase.

DETAILED DESCRIPTION

Molecular Complex

According to a first aspect, the invention therefore relates to a molecular complex that comprises:
  at least one PLL conjugate, comprising:
    a main PLL straight chain, and
    at least one molecule F that has a mean molecular weight of between 50 dalton and 1000 dalton and is linked covalently to said main chain, and
  at least one molecule M that is unstable in solution,
with the conjugate(s) and the molecule(s) M being linked by a non-covalent bond, i.e., interacting by a non-covalent bond.

PLL Conjugate

The PLL conjugate can be monofunctional or polyfunctional. The same complex, if it contains multiple PLL conjugates, can contain only monofunctional conjugates, only polyfunctional conjugates, or a mixture of monofunctional and polyfunctional conjugates. Preferably, the PLL conjugate is monofunctional.

It comprises a main PLL chain and at least one molecule F that has a mean molecular weight of between 50 and 1000 dalton. The molecule(s) F is/are linked covalently to the main chain. The PLL conjugate can consist exclusively of a main PLL straight chain and at least one molecule F that has a mean molecular weight of between 50 dalton and 1000 dalton and is linked covalently to said main chain. The PLL chain has a mean molecular weight that is preferably between 2000 and 300000 dalton, which means that its degree of polymerization (i.e., the value of the index n of the formula provided in the definition part) is between approximately 15 and approximately 2360 lysyl residues.

According to a preferred embodiment of the invention, the PLL chain has—in the molecular complex according to the invention—a mean molecular weight that is in general between 2000 and 300000 dalton, which means that its degree of polymerization is between approximately 15 and approximately 2360, preferably between 20000 and 50000 dalton, which means a degree of polymerization of 155 and 394 or between 155 and 374 lysines. Even more preferably, the PLL chain comprises between 30 and 150 lysines corresponding to a mean molecular weight of between 3800 and 19100 dalton, more preferably between 50 and 100 lysines corresponding to a mean molecular weight for the PLL chain of between 6400 and 13000 dalton.

The main PLL straight chain of the conjugate is preferably a straight alpha chain.

The molecule F preferably has a molecular weight of between 100 dalton and 1000 dalton, even more preferably between 200 dalton and 1000 dalton, in particular between 300 dalton and 1000 dalton, even more particularly between 400 dalton and 1000 dalton, and preferably between 500 dalton and 1000 dalton.

The molecules F are substituents or non-immunogenic molecules. Molecules as described in the patent application PCT WO96/15810 can in particular be used for this invention. The molecules F are preferably selected from one of the following three categories:

molecules with a "fatty acid or lipid" nature, which comprise:
monocarboxylic or dicarboxylic fatty acids, hereinafter usually referred to as (di)fatty acid, with a straight or branched chain, saturated or unsaturated, comprising in general from 4 to 24 carbon atoms;
compounds involved in the anchoring mechanism of proteins with cell membranes, with these compounds intervening in particular in the mevalonate cycle, in particular the isoprenoids linked to a cysteine;
cholesterol and its derivatives, in particular hydrophobic hormones.
molecules with an "antioxidant" nature, which comprise:
vitamin A, vitamin C, vitamin E, or one of the derivatives thereof;
cysteine and its derivatives, of formula: R1S-R2-CH(NH2)-COOH, in which R1 represents H or CH3, and R2 represents a C1-C3 alkylene.
molecules with an "amino acid or neurotransmitter" nature, which comprise:
indolealkylamines;
catecholamines;
the amino acids of formula: R3-CH(NH2)-COOH in which R3 represents hydrogen, an imidazol-2-ylmethyl group, a carboxymethyl group, or an aminopropyl group;
(C1-C5)alkylsulfonic or sulfinic amino acids;
carnitine or carnosine;
the diamines of formula: 2HN-A-NH2 in which A represents a (C1-C6)alkylene or a —(CH2)m-NH—B—(CH2)p- group, in which m and p, independently of one another, are integers ranging from 1 to 5, and B represents nothing or a —(CH2)n-NH— group, with n being an integer ranging from 1 to 5;
acetylcholine and
γ-aminobutyric acid.

Three types of conjugate(s) (whether they be monofunctional or polyfunctional) will therefore be distinguished: the "fatty acid or lipid" conjugates; the "antioxidant" conjugates; and the "amino acid or neurotransmitter" conjugates.

In general, the (di)fatty acid comprises 4 to 24 carbon atoms, such as, for example, the following acids: butyric, maleic, succinic, glutaric, adipic, pimelic, suberic, sebasic, caproic, caprylic, capric, lauric, myristic, palmitic, palmitoleic, stearic, oleic, linoleic, [gamma]-linolenic, [alpha]-linolenic, arachidic, gadoleic, arachidonic, behenic, erucic, or azelaic. Preferably, the acid is selected from among myristic acid, palmitic acid, stearic acid, oleic acid, or (di)acid, azelaic acid, for example.

The isoprenoids that are linked to a cysteine in general comprise from 6 to 20 carbon atoms. Preferably, within the framework of the invention, farnesyl-cysteine, geranyl-geranyl-cysteine, or mevalonate-cysteine is used.

As a hydrophobic hormone, progesterone or 2-methoxyestradiol is preferably used.

As derived from cysteine, homocysteine or methionine is preferably used.

The indolealkylamines and catecholamines used within the framework of the invention comprise in particular tryptophan, 5-methoxytryptophan, serotonin, tryptamine, 5-methoxytryptamine, melatonin, phenylalanine, 3,4-dihydroxyphenylalanine, and tyrosine.

As amino acids, preferably histidine, glycine, and aspartate are used. The amino(C1-C5)alkylsulfonic or sulfinic acids used according to the invention include in particular taurine, homotaurine, and hypotaurine. The diamines that are used in a preferred manner within the framework of the invention are putrescine, cadaverine, spermine, and spermidine.

By way of nonlimiting example, the following can be cited as a PLL conjugate that can be used for the implementation of the invention: oleic acid-PLL, azelaic acid-PLL, and 5-methoxytryptamine-PLL.

Preferably, a cysteine-PLL, a methionine-PLL, a taurine-PLL, a glutathione-PLL or a thioctic acid-PLL will be used. Thus, the molecule(s) F linked covalently to the main PLL chain is (are) selected from among cysteine, methionine, thorine, glutathione, and thioctic acid.

According to a suitable embodiment, the molecular ratio by mass and the area of the peaks between the molecule(s) F and the main chain (determined by FTIR) is between approximately 10 and approximately 20.

Molecule M that is Unstable in Solution

The molecule M is preferably a macromolecule, i.e., a molecule that has a molecular weight that is preferably greater than 1000 dalton, preferably 2000 dalton, even more preferably greater than 5000 dalton, and in particular greater than 10000 dalton. The molecules M can be organic and/or mineral and can be of natural and/or synthetic origin. Preferably, they are organic molecules.

Preferably, the molecules M are useful molecules in the biological systems, preferably useful in the therapeutic, cosmetic, nutritional, and/or diagnostic fields. The molecule(s) M is/are therefore very preferably molecules that have an activity that is pharmacological and/or nutritional and/or cosmetic and/or is a diagnostic reagent.

Preferably, they belong to the family of carbohydrates, proteins, lipids, protides (also referred to as conjugated proteins), such as, for example, lipoproteins, mucoproteins, nucleoproteins, nucleic acids (such as DNA, RNA, interfering RNA, tRNA, cystRNA, etc.), and the metal proteins (example: metalloproteins).

Among the molecules M of carbohydrate type, it is possible to cite the oligosaccharides (sugars composed of 2 to 10 monosaccharide base units), polysaccharides. The examples of molecules M such as oligosaccharide and polysaccharide that can be used in the invention are in particular collagen, cellulose, starch, factor VIII, immunoglobulins.

Among the molecules M of protein type, it is possible to cite in particular the structure proteins that make it possible for the cell to maintain its organization in space; the transport proteins that ensure the transfer of different molecules into and outside of the cells; the regulating proteins that modulate the activity of other proteins or that control the expression of genes; the signaling proteins that collect the outside signals and ensure their transmission into the cell or the body such as, for example, the hormonal proteins; the receptor proteins that detect the messenger molecules and the other signals so that the cell then acts, such as, for example, the sensor proteins and the hormone receptors such as insulin; the motor proteins that make it possible for cells or organisms or certain elements to move or deform such as actin and myosin; the defense proteins that protect the cell against the viruses such as, for example, the antibodies; the storage proteins that make it possible to store amino acids to be able to create other proteins, such as, for example, ovalbumin and enzymes. The examples of molecules M of protein type that can be used in the invention are immunoglobulins, proteins of coagulation, factors VIII and IX, albumin, etc.

Among the molecules M of lipid type, it is possible to cite the saturated and unsaturated fatty acids, the glycerides, (mono, di and tri), and the phospholipids. The examples of molecules M of lipid type that can be used in the invention are lipoproteins, for example the lipoprotein A.

Preferably, the molecule M is a protein.

The molecule(s) M and the conjugate(s) PLL are linked in a non-covalent way by at least one non-covalent bond. A molecule M and a PLL conjugate can be linked by one or more non-covalent bonds.

According to a suitable embodiment, the ratio between the molecular concentration of the conjugate(s) and that of the molecule(s) M is between 1 and 30.

Composition

According to another aspect, the invention also relates to a composition that comprises one or more molecular complex(es) according to the invention in solution in a hydrophilic solvent, preferably selected from among water, a phosphate buffer, physiological serum, or a mixture thereof.

The hydrophilic solvents that are useful for implementing the invention can be varied to the extent that they make possible the solubilization of the molecule(s) M and the conjugate(s) that is/are selected.

The composition can comprise—in addition to molecular complex(es) according to the invention and hydrophilic solvent—at least one other compound. It can be, for example, another pharmaceutically compatible compound that is selected from among an excipient, a surfactant, a vehicle, etc.

Production Method

Synthesis of PLL Conjugates

The methods for coupling between the molecules F and the PLL, for obtaining PLL conjugates according to the invention, are conventional chemical coupling methods that are well known to one skilled in the art, between a functional group of each molecule and the ε-amine functional group of the PLL. These couplings are carried out by means of a coupling agent, selected from among, for example, glutaraldehyde, succinic or glutaric anhydride, the carbodiimides, ethyl chloroformate, or hexamethylene diisocyanate. Examples of such coupling methods are in particular those described in Geffard et al., C. R. *Acad. Sci. Paris:* 295, 797-802, (1982). It is also possible to associate the molecules with the PLL by simple adsorption. Examples of suitable coupling methods are described in detail in the preparations below.

By way of illustration, the coupling between said molecules and the PLL can be carried out between the ε-amine group of the PLL and a carboxylic group of said molecules or other activatable chemical groups.

Thus, in the case of fatty acids, in particular myristic acid, palmitic acid, etc., as well as in the case of isoprenoids linked to a cysteine, in particular farnesyl-cysteine, the bond with the PLL is carried out between an amine group of the latter and the carboxylic group of the above-mentioned molecules.

Likewise, in the case of the cysteine and its derivatives, the bond with the PLL is advantageously made between an amine group of the latter and the acid group of these molecules.

Alternatively, cysteine and its derivatives can be activated in advance by coupling with succinic or glutaric anhydride, with the bond then being made between the ε-amine group of the PLL and the free acid group of the succinylated or glutarylated molecule. Or else cysteine and its derivatives can be linked to the PLL by reaction with glutaraldehyde, with the reaction being done in particular as described by Geffard et al., *Brain Res.:* 294, 161-165, (1984). In the case of cholesterol and its derivatives, the coupling with the PLL is advantageously carried out by means of the hydroxyl group of the cholesterol.

In a variant, cholesterol and its derivatives are adsorbed in the PLL.

In the case of hydrophobic hormones, the coupling with the PLL is advantageously carried out by hexamethylene diisocyanate.

In the case of vitamin A (retinoic acid), the bond between this molecule and the PLL is made between the amine group of the latter and the acid group of the molecule.

In the case of vitamin C (ascorbic acid), the bond between this molecule and the PLL is made between the amine group of the latter and the oxo group of the molecule.

In the case of vitamin E ([alpha]-tocopherol), the bond between this molecule and the PLL is made between the amine group of the latter and the free acid group of the acidic succinate of the molecule.

In the case of aminoalkylsulfonic or sulfinic acids, in particular taurine, homotaurine and hypotaurine, the bond between these molecules and the PLL is made by activation in advance of the molecules with a (succinic or glutaric) acid anhydride, or else by coupling with glutaraldehyde.

In the case of amino acids, certain indolealkylamine compounds, in particular tryptophan and catecholamines, it is possible to make the bond between these molecules and the PLL either directly or by coupling with carbodiimide, glutaraldehyde, an acid anhydride, or an acid chloride, for example ethyl chloroformate.

In the case of diamines, it is possible to make the bond between these molecules and the PLL by coupling with glutaraldehyde or an acid anhydride. The bond between the carnitine or the carnosine, on the one hand, and the PLL, on the other hand, is made by coupling with carbodiimide.

Method for Obtaining the Molecular Complex According to the Invention

The molecular complex according to the invention can be obtained by a method that comprises the following steps:
delivery of one or more PLL conjugates, comprising:
a main PLL straight chain, and
at least one molecule F that has a mean molecular weight of between 50 dalton and 1000 dalton and is linked covalently to said main chain, and
delivery of one or more molecules M,
bringing conjugate(s) into contact with the molecule(s) M under conditions that make it possible to form non-covalent bond(s) between the conjugate(s) and the molecule(s) M.

The step of delivery of the conjugate(s) preferably comprises the delivery of a solution that comprises the conjugate(s) in a hydrophilic solvent.

In a preferred way, the step for ensuring contact is carried out at a temperature of between approximately 4° C. and 25° C. and in a buffered solution.

Likewise, the step for delivery of the molecule(s) M preferably comprises the delivery of a solution that comprises the molecule(s) M in a hydrophilic solvent.

According to a particularly suitable embodiment, the time period for bringing the conjugate(s) into contact with the molecule(s) M is between 1 hour and 24 hours.

Uses of the Molecular Complex

The molecular complexes or the compositions containing them can be used for various applications, linked in particular to the nature and the effectiveness of the molecules M.

In the case of a molecule M that has a pharmacological activity, i.e., a pharmacological active ingredient, the molecular complex according to the invention can be used as a medication.

Preferably for this use, the molecular complex is administered within a composition, in particular a composition according to the invention.

The molecular complex according to the invention is preferably administered intravenously, intramuscularly, subcutaneously, or orally, by nasal spray, by mouth or by ear, or cutaneously and by ophthalmic solution.

Advantageously, the complexes of the invention retain or improve the original pharmacological activity of the molecule M. The presence of PLL-based conjugates therefore does not affect this ex-vivo (or in-vivo) activity. It has also been demonstrated that their presence is not detrimental to the action of the molecule M in vivo (i.e., after administration to a patient).

Furthermore, and against all expectations, the presence of conjugates also has a beneficial effect on the pharmacological activity of the molecule M by improving its bioavailability.

It is therefore possible to use complexes of the invention comprising a molecule M for therapeutic purposes as a medication and in methods for treating the human body or animals by therapy, surgery, or else in diagnostic methods.

The nature of the treatment will depend quite obviously on the type of pharmacological activity of the complexed molecule M.

By way of example, it is possible to cite the treatment of hemostasis problems.

The complexes according to the invention can also be used for the purpose of improving the taste or texture of food, reducing the lipid content, or encapsulating nutrients, for example vitamins in foods, so that they do not degrade over the shelf life. Furthermore, they can be used for the purpose of manufacturing packaging that makes it possible to preserve food for longer periods.

Use of Conjugates for Stabilizing Molecules that are Unstable in Solution

The invention also has as its object the use of at least one PLL conjugate, comprising:
a main PLL straight chain, and
at least one molecule F that has a mean molecular weight of between 50 dalton and 1000 dalton and is linked covalently to said main chain, and
in a hydrophilic solution, for:
improving the hydrophilic nature, and/or
improving the stability in solution, and/or
improving and/or keeping in solution the pharmacological and/or nutritional and/or cosmetic and/or diagnostic activity of a diagnostic reagent
of a molecule M that is unstable in solution, by forming a molecular complex according to the invention by a non-covalent bond.

If the molecule M is an active pharmaceutical substance, maintaining the pharmacological activity of the molecule M in solution preferably corresponds to a variation of the pharmacological activity of at least 5% in relation to the initial pharmacological activity at a temperature of at least 1° C. for 1 hour.

According to a variant, the purpose of the invention is also the use of at least one PLL conjugate, comprising:
a main PLL straight chain, and
at least one molecule F that has a mean molecular weight of between 50 dalton and 1000 dalton and is linked covalently to said main chain, and
in a hydrophilic solution that contains a molecule M that is unstable in solution and undesirable in said solution, to form a molecular complex according to the invention by a non-covalent bond and to decontaminate said solution.

The invention also has as its object a kit for implementing these uses. This kit comprises at least one hydrophilic solution that comprises at least one PLL conjugate that comprises:
a main PLL straight chain, and
at least one molecule F that has a mean molecular weight of between 50 dalton and 1000 dalton and is linked covalently to said main chain.

Identification Method

The purpose of the invention is also a method for identification of at least one PLL conjugate that can be linked in a non-covalent way to a molecule M that has a pharmacological activity, unstable in solution, and that can maintain the pharmacological activity of said molecule M in a hydrophilic solution, with said method comprising:
a) the delivery of a molecule M that is unstable in solution and that has a pharmacological activity;
b) the delivery of at least one molecular complex that comprises said molecule M according to the invention;

c) the comparison between the initial pharmacological activity and the pharmacological activity of said molecular complex(es) comprising the molecule M;
d) the identification of one or more molecular complexes whose pharmacological activity in solution in the liquid phase is maintained after the solubilization;
e) the identification of a PLL conjugate or a combination of multiple PLL conjugates that make possible said maintaining of the pharmacological activity.

The molecular weight of the molecule M is preferably greater than 1000 dalton.

In a preferred way, step c) for comparison is carried out between the initial pharmacological activity of the molecule M and the pharmacological activity of the molecular complex(es) that are measured multiple times at time intervals that are determined starting from the formation of the complex(es), at least every 24 hours.

Preferably, step d) for identification of the complex(es) also comprises:
the comparison of the change in pharmacological activity of each tested molecular complex depending on time;
the identification of the complex(es) of which the variation in pharmacological activity is at least 5% in relation to the reference pharmacological activity of said macromolecule at a temperature of at least 1° C. for at least 1 hour.

The identification method according to the invention therefore preferably comprises at least three steps:
the study of the solubility of the conjugated macromolecule complex(es) in solution,
the verification that the macromolecule well retains its original pharmacological activity, and
the monitoring of the pharmacological activity of the macromolecule complex(es)-soluble conjugate(s), i.e., having "validated" the preceding step over time.

An in-silico analysis such as the one described above is optional but advantageous in most cases because it makes it possible to restrict relatively quickly the number of possible conjugates in the formation of soluble complexes and therefore to simplify the monitoring of the identification analysis.

The solubility of the macromolecule in the presence of the conjugate(s) or their mixtures (optionally selected by the in-silico analysis method) is studied in liquid solution. The methods that are used to determine such a solubility are standard and known to one skilled in the art. It will nevertheless be possible to cite an analysis by measurement of the optical density or any method of pharmacopoeia known to one skilled in the art.

The preferred solvents for implementing the method according to the invention are the physiologically compatible solvents that are preferably hydrophilic and preferably also aqueous such as distilled water, phosphate buffers, and physiological serum. Other solvents, such as the C1-C3 alcohols or dimethyl sulfoxide (DMSO), can be present and their total quantity therefore in general does not exceed 10% by volume in relation to the total volume of the complex solution.

As a general rule, the insolubility of a molecule in solution is quickly visible to the naked eye, in a period on the order of several seconds to several minutes in certain cases. Consequently, a simple visual study of the samples of different complexes in solution could suffice to determine the solution(s) of complexes that can be suitable for the second step of temporal analysis of activity.

However, optical density analyses, for example, make it possible to obtain a more precise measurement of this phenomenon.

The original activity of the soluble complexes is first of all verified, and then the activity is next measured at different time intervals starting from the formation of said complex(es), preferably every hour, more preferably every 24 hours, and then every 3-4 days.

For a molecule for therapeutic purposes, the measurement of the pharmacological activity can be done starting from any suitable analysis method without any limitation. These analysis methods are well known to one skilled in the art and their use depends essentially on the nature of the macromolecule of interest for therapeutic purposes. By way of example, when the macromolecule is an antibody, it will be possible to use any method that makes it possible to evaluate its affinity with its antigen and its analogues, such as the immuno-enzymatic methods. When the macromolecule is a DNA or RNA sequence, for example, it will be possible to use the MALDI-TDF spectrometry method, electrophoresis or high-performance liquid chromatography (HPLC).

When the molecule M does not have a particular therapeutic purpose, such as, for example, the natural or synthetic polymers, the resins, and other polymer additives, it is no longer possible, of course, to speak of pharmacological or biological activity, but the method as described above will be implemented by replacing the pharmacological activity by the characteristic(s) or property(ies) of the molecule M. All that is described in this application with reference to the pharmacological activity of a macromolecule for therapeutic purposes also applies with reference to the characteristics or properties of a non-therapeutic molecule M of interest.

According to another aspect, the invention relates to a kit for the determination of a conjugate or a combination of multiple conjugates that make it possible to maintain the pharmacological activity of one or more macromolecule(s) in solution, preferably in the liquid phase, comprising at least two monofunctional or polyfunctional conjugates that are identical or different or at least two mixtures of monofunctional or polyfunctional conjugates that are identical or different, and in which each of said conjugates comprises a main alpha-PLL-type straight chain and one or more molecules that each have a molecular weight of at least 50 dalton and at most 1000 dalton linked covalently to said main chain.

The kit according to the invention can comprise at least two conjugates or mixtures of PLL conjugates as defined above, preferably between two and ten.

The chemical nature of the PLL conjugates that can be included in the kit according to the invention is as described in this application.

According to a variant, the kit according to the invention comprises PLL conjugates or mixtures of conjugates packaged in separate containers. The containers that can be used are, for example, disposable flasks or doses.

The kit makes it possible to make a rapid screening by the laboratory for the selection of the PLL-F1 and PLL-F2 compound that best corresponds to the stability research.

Stability and measurement of effectiveness will complete the analysis and will make it possible to validate whether or not the macromolecule is "treatable" with a PLL-F compound and to orient the compounds that will be grafted by non-covalent bonds.

EXAMPLE AND EXPERIMENTS

The remarkable properties of the complexes according to the invention have been demonstrated by the experiments described below.

Equipment and Methods

"In-Silico" Study

The "in-silico" analysis is an analysis that is carried out completely by means of a computer and Pymol software. It makes it possible to determine and to select the particular PLL conjugates that can interact with a given molecule M depending on the distribution of polar amino acids and therefore depending on the charges of the molecule M.

The sources that are used are as follows:
Human Proteins: Pubmed/Protein Data Base/Uniprot
Immunoglobulin of Isotypy G: Saphire, E. O. et al. Crystal Structure of a Neutralizing Human IGG Against HIV-1: A Template for Vaccine Design. Science. 2001
Coagulation Factor VIII: Ngo, J. C. et al. Crystal Structure of Human Factor VIII: Implications for the Formation of the Factor IXa-Factor Villa Complex Structure. 2008
Coagulation Factor IX: Wang, S. et al. Studies of Benzothiophene Template as Potent Factor IXa (FIXa) Inhibitors in Thrombosis. J. Med. Chem. 2010
Hemoglobin: Safo, M. K. et al. The Enigma of the Liganded Hemoglobin End State: A Novel Quaternary Structure of Human Carbonmonoxy Hemoglobin. Biochemistry 2005.
Albumin: Bhattacharya, A. A. et al. Binding of the General Anesthetics Propofol and Halothane to Human Serum Albumin. High Resolution Crystal Structures. 2000) J. Biol. Chem.

The software that is used for the study of protein structures is pymol (pymol.org/).

"Sedimentation"

In biochemistry, the sedimentation is the separation of proteins in solution that have the ability to sed out in a high centrifugal field.

Ultracentrifuging is practiced and in this case, the molecules are put into motion and sed out as a result of their density, which is higher than that of the solvent. It is therefore possible to determine different macromolecules and their molar mass as well as their sedimentation constant that is measured in svedberg units (S).

"Centrifuging"

Centrifuging is a method for separating compounds from a mixture depending on their difference in density by subjecting them to a centrifugal force.

The apparatus that is used is a high-speed rotating machine called a centrifuge.

During this separation operation, the compounds in the fluid that are located at a distance r from the axis of rotation are subjected to different forces:
the downward force of gravity Fp
the upward Archimedes' force Fa
a friction force Fv
the centripetal force F'c
the centrifugal force Fc The separation is performed by the action of the centrifugal force Fc on the compounds. This centrifugal force, expressed in newtons, is provided by the equation $Fc=m\gamma c$ with $\gamma c=r\omega^2$ in m/s$^2$, including:
the mass m of the compound that is to be separated
the distance r from the tube to the axis of rotation of the centrifuge
the angular speed ω expressed in radians per second or in rpm.

The ratio of the centrifugal force Fc to the weight Fp is called intensity of the artificial gravity and is expressed in "G"3. The values that are used in centrifuging are from approximately 400 to 10000 G, which corresponds to speeds of rotation on the order of 2000 to 10000 rpm, according to the radius of the rotors.

Certain applications like the separation of the biological macromolecules (proteins, nucleic acids) require the ultracentrifuging method developed by Svedberg, which uses very high artificial gravity intensities on the order of 200000 G, and which thereby requires speeds of rotation of several tens of thousands of rpm.

"Optical Density"

The absorbency or optical density measures the capacity of a medium to absorb the light that passes through it.

The absorbency differs according to the nature of the substance under study, according to the wavelength under which it is analyzed, and according to the concentration of this substance in the medium that is passed through. This medium can be solid, liquid, or gaseous, provided that it is transparent. It is measured by a spectrophotometer. The Beer-Lambert Law establishes a proportionality between the concentration of a chemical entity in solution (or the partial pressure of this entity in the gas phase), the absorbency of the former, and the length of the path traveled by the light in the solution.

The concentration is expressed in mol·L$^{-1}$ or in mol·m$^{-3}$.

"ELISA"

ELISA is a biochemical technique that uses one or two antibodies. One of the former is specific to the antigen, while the other reacts to the immune complexes (antigen-antibody) and is coupled to an enzyme. This secondary antibody can also cause the emission of a signal by a chromogenic substrate or fluorophore.

The "ELISA" protocol within the framework of the invention is as follows:

Experiments of "Title" and "Affinity":

Sensitization of the "Maxisorp" Wells:

Each well receives 200 μl of a 0.05 M (pH=9.6) carbonate buffer solution that contains antigen at the concentration of 10 μg/ml. Monitored wells are produced with the carrier protein that is modified by the coupling agent at the same concentration. The plates are stirred for 16 hours at 4° C.

Saturation:

The plates are emptied and then filled with 200 μl of "2.5 g/l PBS-Tw bovine serum albumin (BSA)" buffer. The plates are incubated for 1 hour at 37° C.

Washing Cycles:

The plates are emptied and washed 3 times with PBS-Tw.

Incubations of the Antibodies:

The antibodies are diluted in different buffers:
the control buffer: the same as the saturation buffer
the "tests" buffer: this is the saturation buffer that contains a PLL-F compound.

Thus, three solutions, i.e., three different concentrations ($10^{-4}$M, $10^{-5}$M, and $10^{-6}$M) have been tested by the PLL-F conjugate.

The tested PLL-F are as follows:
methionine-G-PLL
glutathione-G-PLL
taurine-G-PLL
cysteine-G-PLL The thus diluted antibodies are deposited on the plate at a rate of 200 μl per well. This test comprises a dilution study of the antibody (1:2500 to 1:80000) and an affinity study (dilution 30 of the antigen of $1.10^{-6}$ to $1.10^{-12}$ M).

The dilution study of the antibody makes it possible to determine the antibody concentration and therefore to determine the antibody dilution to be used for the affinity and specificity study. [Mangas et al. *Chapter* 1. *Brain Molecules: From Vit to Molecules for Axonal Guidance.* 2008].

The absence of a signal at the end of the ELISA test (A) indicates that all of the antibody sites recognize the target, i.e., there is a high affinity for the target. A high signal at the end of the test (B) is interpreted as a low affinity of the antibody for the antigen. [Mangas et al. *Chapter* 1. *Brain Molecules: From Vit to Molecules for Axonal Guidance.* 2008].

Washing Cycles:

The plates are emptied and washed 3 times with PBS-Tw (Tw=tween)

Incubation of the Secondary Antibodies:

The wells receive 200 µl of "2.5 g/l BSA, PBS-Tw" buffer containing immunoglobulins that are directed against the IgG of the host radical marked with peroxydase and diluted with 1/10000. The plates are incubated for 1 hour at 37° C.

Washing Cycles:

The plates are emptied and washed 3 times with PBS-Tw.

Revealing:

The wells receive 200 µl of revealing buffer (50 mM of citrate, 100 mM of phosphate, 0.03% H2O2, pH5), diluted with 0.2% orthophenylene diamine.

The coloring is allowed to develop in darkness for 10 minutes, and the reaction is stopped using 50 µl of 2N HCl per well.

The optical density is then read at 492 nm.

"Dot Blot"

In a "dot blot," the nucleic acids (DNA or RNA) or the proteins are transferred from a liquid medium directly to a membrane, without prior separation. The transfer can be carried out by simple diffusion, by diffusion in an electrical field (electrodiffusion), or by vacuum suction.

The detection is similar to those used in the transfers with separation: for example, sequences of nucleotides for DNA or RNA or antibodies for proteins.

"Dot Blot" Protocol within the Framework of the Invention:

By way of example, a mouse monoclonal antibody (AcM) was taken as a model: anti-11DehydroThromboxane B2 (11DHTB2-BSA), clone 2E1-B4 (IgG1, K) (cell supernatant).

The corresponding antigenic compound: anti-11Dehydro-Thromboxane B2-BSA.

Sensitization of the Nitrocellulose Membrane:

Transfer of the antigen from a liquid medium directly to a membrane, by vacuum suction. Each well receives 200 µl of a Tri-NaCl (TBS) 1× buffer solution that contains antigen. Control wells are made with the carrier protein modified by the coupling agent at the same concentration.

The system is placed under vacuum at ambient temperature for 1 hour.

Saturation:

Removing the membrane and making light cuts for delimiting the future "deposition bands." Then, immersing the membrane in the "TBS 1×-TW, 1% BSA" saturation buffer for 1 hour at ambient temperature while being stirred.

Washing Cycles:

The membrane is then washed once with TBS 1×.

Incubation of the Antibodies:

Cutting the membrane into deposition bands. Each band is immersed in a solution that contains the antibody at a given dilution at 4° C. for 16 hours. That is to say, the antibodies are diluted in different buffers:

the control buffer: the same as the saturation buffer
the "tests" buffer: this is the saturation buffer that contains a PLL-F compound. Thus, three solutions, i.e., three different concentrations ($10^{-4}$M, $10^{-5}$M, and $10^{-6}$M) were tested by the PLL-F compound.

The tested PLL-F are the following:
methionine-G-PLL
glutathione-G-PLL
taurine-G-PLL
cysteine-G-PLL This test makes it possible to study the influence of the PLL-F compound on the Ag/Ac interaction by following the density of the dot-blot "spot."

Washing Cycles:

The bands are washed 3 times with 0.005% TBS1×-TW.

Incubation of the Secondary Antibodies

The bands are immersed in the TBS1×TW (0.005%)-BSA (0.1%) buffer containing immunoglobulins directed against the IgG of the host radical marked with peroxydase and diluted with 1/5000 for 1 hour at ambient temperature while being stirred.

Washing Cycles:

The bands are washed 3 times with 0.005% TBS1×-TW and a last washing cycle with TBS1× is done to remove the foam.

Revealing:

The bands are immersed in the revealing buffer. The coloring develops in darkness for 10 minutes, and the reaction is stopped using 50 µl of 2N HCl per band. The intensity of the spots is estimated by the experimenter.

"Cell Counting"

The method that is used is the method of counting by Malassez Cell and trypan blue. Trypan blue is a negatively-charged chromopore reagent (blue color) that does not interact with the membrane if the latter is intact. It will therefore color only the damaged cells, making it possible to determine the viability of a sample. The samples are diluted and then mixed with trypan blue. Once placed on a conventional counting cell (Malassez Cell), the total cell number is determined and then the cells that appear in the color blue (cells with damaged membranes) are in turn counted. The biomass is determined from the total number of cells, while the viability is determined starting from this formula:

$$\text{Viability} = [n(\text{blue cells})/n(\text{total})] \cdot 100\%$$

A Malassez cell is a special checkered lamina that makes it possible to count different types of cells.

The entire Malassez cell consists of 100 rectangles whose dimensions are: length=0.25 mm/width=0.20 mm/depth=0.20 mm. The total volume of the cell is 1 mm3 (100×2.5×0.2×0.20). The checkering therefore consists of 10 vertical bands (0.25 mm) and 10 horizontal bands (0.20 mm) thus forming 100 rectangles.

The cells are only counted in 10 of the 25 random non-contiguous rectangles in the cell.

The number of cells present in each rectangle is totaled. Arbitrarily, it is agreed to take into account only cells positioned on the right and lower sides.

The mean number of cells per rectangle (total of the cells observed in 10 rectangles divided by the number of rectangles that are counted) is calculated. The number that is obtained is multiplied by 100 to know the number of cellular entities per mm$^3$.

"FTIR"

The Fourier transform infrared (FTIR) spectrometer is an analysis tool that is widely used for the identification and the quantification of molecules and proteins. The main region of the vibrational spectroscopy is the infrared mean (4000 to 400 cm$^{-1}$) of the electromagnetic spectrum. The wave number is defined by the inverse of the wavelength, expressed in centimeters. The spectroscopy can be defined as the study of the interaction of an electromagnetic wave with the material. Thus, this technique makes it possible to identify the chemical functional groups of any molecule via the vibrations that are characteristic of its chemical bonds. The result that is achieved is an IR spectrum of the molecule under study, either in transmittance mode or in absorbance mode, where the peaks can be interpreted using frequency correlation tables of the valence vibrations. The analyses carried out on the poly-L-lysine conjugates make it possible to verify the grafting of small molecules onto the PLL (shift on the peaks of the amide of the PLL) and to determine the specific peaks with small grafted molecules. A modification of the spectral appearance of a mixture of PLL-F and molecule M, in comparison with the original spectra of the PLL-F conjugate and molecule M, is observed.

Synthesis of the Conjugates According to the Invention

The synthesis of the conjugates according to the invention was carried out in accordance with the methods and indications described in the patent application WO9615810.

Below, the molecules with a molecular weight of at least 50 dalton and at most 1000 dalton linked covalently to the main chain of the PLL will be referred to as "molecules F."

For the purpose of simplifying notation, the conjugates according to the invention are identified by the abbreviation: "molecule F"-"coupling type"-PLL.

For example, the "cysteine-G-PLL" conjugate corresponds to a cysteine that is grafted onto a PLL by means of a spacer arm (or linker, in English terminology) of the glutaraldehyde type. The "orotyl-PLL" conjugate, for its part, corresponds to the orotic acid that is grafted onto a PLL by means of an acid-chloride-type linker.

General Synthesis Procedure

In a general manner, two types of activation relate to the molecules F, according to their molecular family (amino acids or the like): synthesis by activation with glutaraldehyde and synthesis by activation by an acid chloride.

The molecules F that are activated via the synthesis path of glutaraldehyde and grafted onto the PLL follow the following reactions:

$1^{st}$ Step: Condensation Reaction and Formation of Imines

$2^{nd}$ Step: Reduction of Unstable Imines

Each molecule F is activated via the glutaraldehyde (G), which acts as a coupling agent by activating the amine group of the small molecule. The condensation reaction forms imines. This intermediate compound, small molecule and coupling agent, is linked to the epsilon-amine group of the lysyl residue of the poly-L-lysine, forming an amide bond. The unstable imines are stopped by sodium borohydride. This product is purified by dialysis in buffer solutions.

By way of example, it is possible to cite the synthesis of the cysteine-G-PLL compound. The method comprises the implementation of the following steps:
weighing of the cysteine: 400 mg
solubilization in an acetate buffer: 20 ml
activation by 5% glutaraldehyde: 6 ml
grafting onto the PLL: 10 ml
reduction of the imines by 5M $NaBH_4$: 2 ml
purification by dialysis The molecules F that are activated via the synthesis path of ethyl chloroformate and that are grafted onto the PLL follow the following reactions:

Each molecule F is activated via ethyl chloroformate (ECF), which acts as a coupling agent by activating the carboxylic group of the small molecule. This intermediate compound, small molecule and coupling agent, is linked to the epsilon-amine group of the lysyl residue of the poly-O-lysine, forming an amide bond. This product is purified by dialysis in buffer solutions.

By way of example, it is possible to cite the synthesis of the orotyl-PLL compound. The method comprises the implementation of the following steps:
weighing of the orotic acid: 400 mg
solubilization in methanol: 20 ml
addition of triethylamine: 0.4 ml
activation by ethyl chloroformate: 0.25 ml
grafting onto the PLL: 10 ml
purification by dialysis Characterization of the Conjugates According to the Invention The characterization of the conjugates according to the invention has been carried out by the analytic technique of the Fourier transform infrared (FTIR). This spectroscopic technique makes it possible to identify the grafting and the specific peaks of the small molecule on the PLL. Although this method is in general very effective, other methods can also be used, such as, for example, NMR, or the light dynamization or crystallography.

Examples of conjugate characterization according to the invention are reproduced in FIGS. 1A to 1E.

Formation of the Complexes of the Invention

General Procedure

The conjugate(s) according to the invention that is/are synthesized in the previously-described step and the macromolecule of interest are introduced into a reactor, with immobilization in nitrogen, if necessary, according to the protocol that is specific to the molecule M (cf. 4)

Formation of a Complex According to the Invention Comprising a Mouse Monoclonal Antibody (AcM)

In this example, the molecule M is a mouse monoclonal antibody (AcM).

For the in-vitro study, the conditions are as follows:

The AcM (cell supernatant): anti-11DehydroThromboxane B2 (11DHTB2-BSA), clone 2E1-B4 (IgG1, K)

The corresponding antigenic compound: anti-11Dehydro-Thromboxane B2-BSA.

AcM dilution buffer:
TBS1×control buffer
Tested PLL-F compounds: i.e., control buffer+PLL-F
cysteine-G-PLL (10-4M, 10-5M, and 10-6M)
methionine-G-PLL (idem)
glutathione-G-PLL (idem)
taurine-G-PLL (idem)

Formation of a Complex According to the Invention Comprising Factor VIII

In this example, the molecule M is factor VIII.

Factor VIII plays a central role in the coagulation. It is the co-factor of factor IX. Factor VIII, activated via thrombin, becomes the catalyst of the reaction for activation of factor X by the activated factor IX, in the presence of a calcium ion and phospholipids. The reaction for activation of factor X is accelerated approximately 200000 times in the presence of factor VIII.

The activated factor X acquires a catalytic activity that makes it possible for it to transform the prothrombin into thrombin. The former degrades the fibrinogen into fibrin. The thus formed clot will be stabilized by factor XIII, which makes it possible to stop the bleeding.

Also called Christmas factor or anti-hemophiliac factor B, factor IX is one of the essential participants in blood coagulation. The protein (57-kDA vitamin K-dependent procoagulant glycoprotein), coded by the gene F9, is in the inactive state in the blood circulation. When a vessel is damaged, foreign elements infiltrate. As soon as it comes into contact with one of them, it is activated and allows the synthesis of an enzyme, thrombokinase, which takes place in the series of reactions of the coagulation ending in the formation of a blood clot. In the event that this factor IX is absent, the individuals suffer from hemophilia B.

In-Silico Study

Figure 1A:
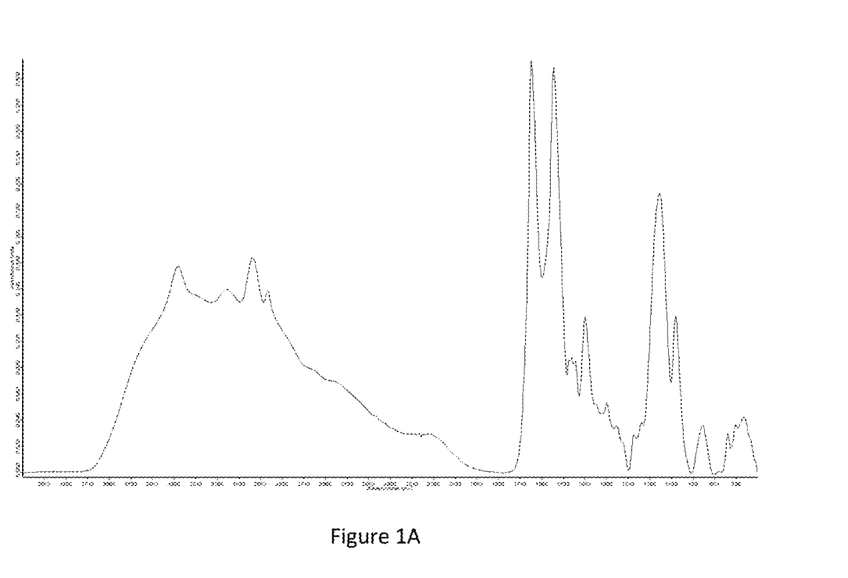
FIG. 1A shows the FTIR spectrum obtained for the cysteine-G-PLL conjugate according to the invention; in this figure, it is possible to observe the PLL that is identified by the 1700-1550 $cm^{-1}$ zone and the cysteine that is indicated by the peaks at around 1300 and 700 $cm^{-1}$.
Figure 1B:
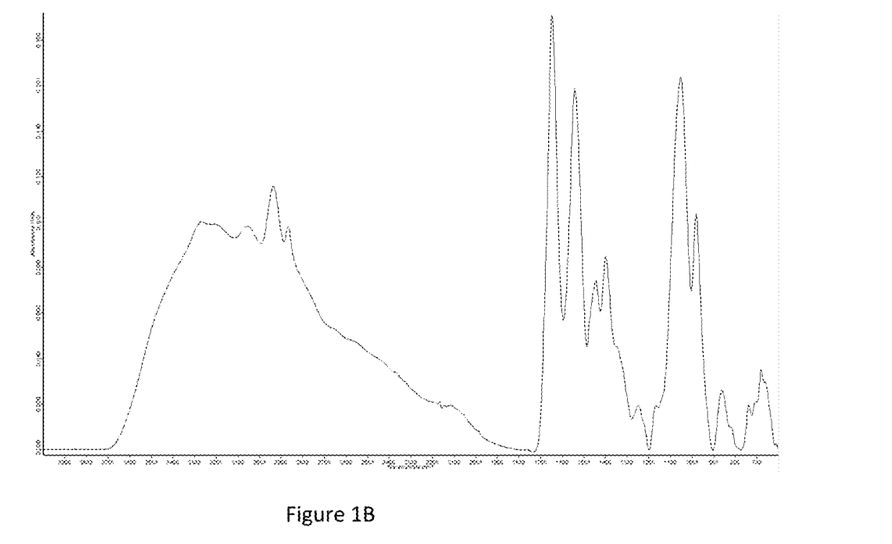
FIG. 1B shows the FTIR spectrum obtained for the methionine-G-PLL conjugate according to the invention; in this figure, it is possible to observe the PLL that is identified by the 1700-1550 $cm^{-1}$ zone and the methionine that is indicated by the peaks at around 1300, 900, and 700 $cm^{-1}$.
Figure 1C:
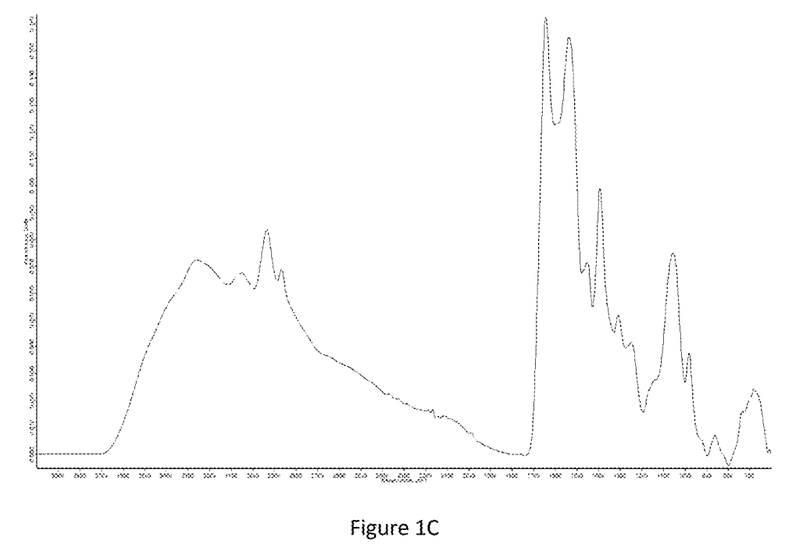
FIG. 1C shows the FTIR spectrum obtained for the glutathione-G-PLL conjugate according to the invention; in this figure, it is possible to observe the PLL that is identified by the 1700-1550 $cm^{-1}$ zone and the glutathione that is indicated by the peaks at around 1300 and 1200 $cm^{-1}$.
Figure 1D:
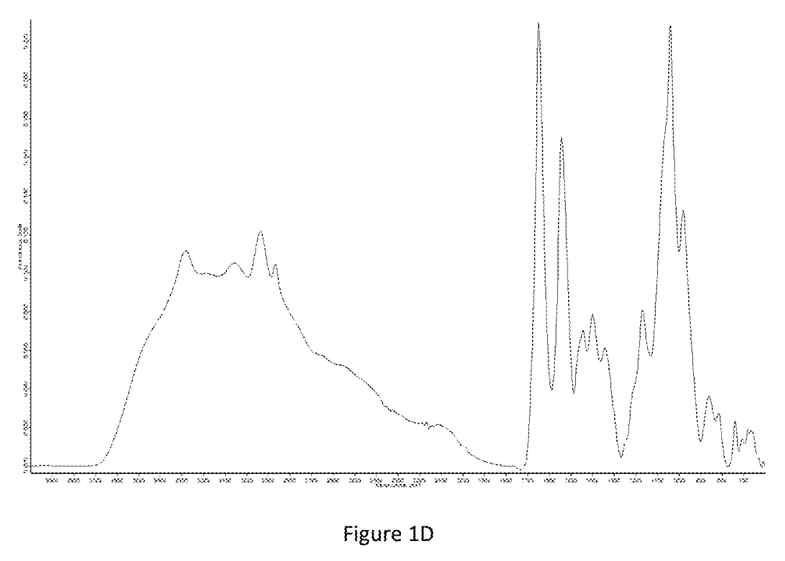
FIG. 1D shows the FTIR spectrum that is obtained for the taurine-G-PLL conjugate according to the invention; in this figure, it is possible to observe the PLL that is identified by the 1700-1550 $cm^{-1}$ zone and the taurine that is indicated by the peaks at around 1300, 1000 and 700 $cm^{-1}$.
Figure 1E:
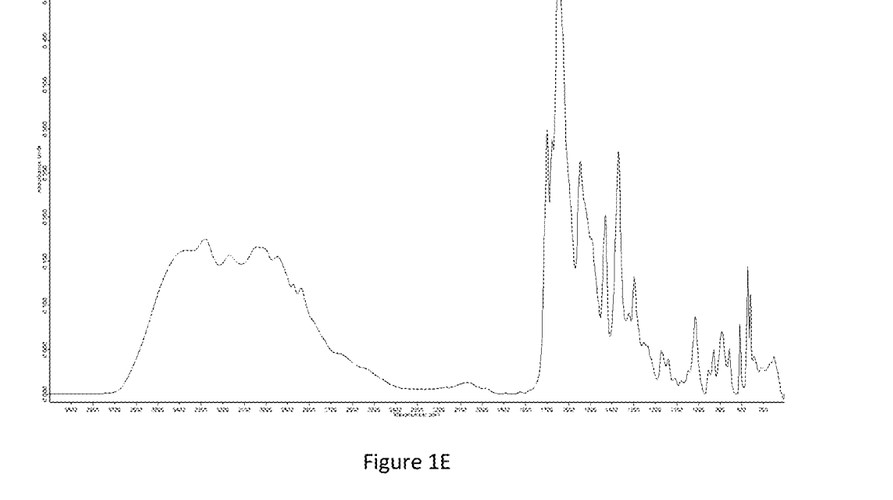
FIG. 1E shows the FTIR spectrum that is obtained for the orotyl-PLL conjugate according to the invention. In this figure, it is possible to observe the PLL that is identified by the 1700-1550 cm$^{-1}$ zone and the orotyl that is indicated by the peaks at around 1300 and 800 cm$^{-1}$.
Figure 2:
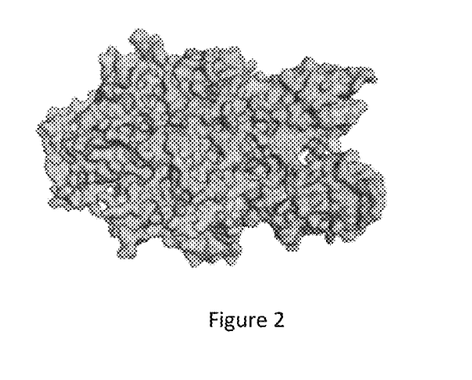
FIG. 2 shows the protein structure of factor VIII by in-silico study.

The protein structure of factor VIII is shown in FIG. 2.

The software makes it possible to display in color in the 3D structure shown in FIG. 2:
- the amino acids with a polar side chain without an acid-base group: serine, asparagine, threonine, glutamine
- the amino acids with a polar side chain with an anionic acid-base group: aspartate, glutamate
- the amino acids with a polar side chain with a cationic acid-base group: lysine, arginine
- the amino acids with a polar side chain with a neutral acid-base group: cysteine, tyrosine, histidine The table below shows the number of groups disclosed by this method.

| Factor VIII | AA without an Acid-Base Group | AA Anionic Acid-Base Group | AA Neutral Acid-Base Group | AA Cationic Acid-Base Group |
|---|---|---|---|---|
| Total Number | 218 | 123 | 122 | 121 |
| Number of Surface Residues | 135 | 96 | 79 | 101 |

| Factor VIII | Total | Representation in % in Relation to the Total of the AA |
|---|---|---|
| Total Number | 584 | 40 |
| Number of Surface Residues | 411 | 28 |

Formation of a Complex According to the Invention Comprising a Hemoglobin

In this example, the molecule M is a hemoglobin.

The activity of the hemoglobin is measured by saturation in oxygen. The human hemoglobin consists of four identical chains, two by two: two α chains of 141 amino acids each, and two β chains of 146 amino acids each (which gives a total of 574 amino acids for the hemoglobin). Each of these chains is associated with a prosthetic group: heme. It is symbolized by "Hb." A heme molecule consists of an iron ion complexed by a porphyrin.

In-Silico Study

Figure 3:
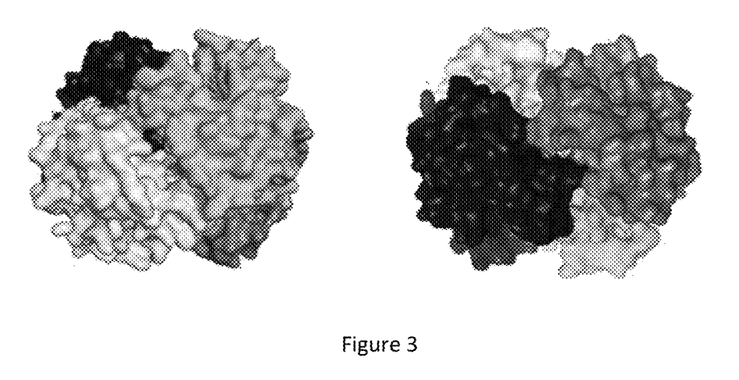
FIG. 3 shows the protein structure of hemoglobin by in-silico study.

The protein structure of the hemoglobin is shown in FIG. 3.

The software makes it possible to display in color in the 3D structure shown in FIG. 3:
- the amino acids with a polar side chain without an acid-base group: serine, asparagine, threonine, glutamine
- the amino acids with a polar side chain with an anionic acid-base group: aspartate, glutamate
- the amino acids with a polar side chain with a cationic acid-base group: lysine, arginine
- the amino acids with a polar side chain with a neutral acid-base group: cysteine, tyrosine, histidine The table below shows the number of groups disclosed by this method:

| Hemoglobin | AA without an Acid-Base Group | AA Anionic Acid-Base Group | AA Neutral Acid-Base Group | AA Cationic Acid-Base Group |
|---|---|---|---|---|
| Total Number by Category | 92 | 54 | 56 | 56 |
| Number of Surface Residues | 92 | 50 | 42 | 50 |

| Hemoglobin | Total | Representation in % in Relation to the Total of the AA |
|---|---|---|
| Total Number by Category | 258 | 45 |
| Number of Surface Residues | 234 | 41 |

Formation of a Complex According to the Invention Comprising an Albumin

In this example, the molecule M is an albumin.

Human serum albumin is one of the most abundant proteins in the circulatory system. It plays a key role in the transport of fatty acids, metabolites, and medications and greatly stimulates the distribution of medications in the body. Without a protein for distributing medications such as antibiotics, it would be much more difficult to combat illness; human albumin makes it possible for certain active substances to bond and to be transported in the entire body. The structure of the human albumin represents a quaternary model. The molecular weight of the protein is 67000, with 585 amino acids. The protein has approximately 67% of the alpha-helix and, surprisingly, no β layer.

Its structure makes it possible to bond to a large variety of natural and synthetic molecules. The human albumin is involved in maintaining the colloidal osmotic pressure. The colloidal osmotic pressure is a form of pressure that should be applied to prevent the excessive quantity of water through the semi-permeable membrane.

In-Silico Study

Figure 4:
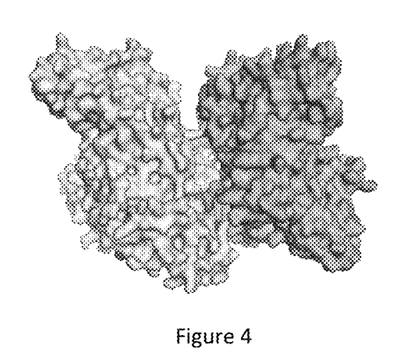
FIG. 4 shows the protein structure of albumin by in-silico study.

The protein structure of the albumin is shown in FIG. 4.

The software makes it possible to display in color in the 3D structure shown in FIG. 4:
- the amino acids with a polar side chain without an acid-base group: serine, asparagine, threonine, glutamine
- the amino acids with a polar side chain with an anionic acid-base group: aspartate, glutamate
- the amino acids with a polar side chain with a cationic acid-base group: lysine, arginine
- the amino acids with a polar side chain with a neutral acid-base group: cysteine, tyrosine, histidine The table below shows the number of groups disclosed by this method:

| HAS | AA without an Acid-Base Group | AA Anionic Acid-Base Group | AA Neutral Acid-Base Group | AA Cationic Acid-Base Group |
|---|---|---|---|---|
| Total Number | 89 | 96 | 68 | 82 |
| Number of Surface Residues | 75 | 83 | 51 | 80 |

| HSA | Total | Representation in % in Relation to the Total of the AA |
|---|---|---|
| Total Number | 335 | 57% |
| Number of Surface Residues | 289 | 49% |

Examples of Analysis of Stability and Solubility in Solution and in Cell Culture a. Stability of Immunoglobulins (Ig) in Aqueous Solution in Different Buffers for Therapeutic Applications For this purpose, PLL-F compounds are used. Two approaches are applied:
- "in-silico" study by the bibliographic research and the study of the structure of the Ig
- "in-vitro" study by the ELISA/Dot Blot technique:
  direct "binding"
  affinity
  specificity b. Stability of Monoclonal Hybridomas in Aqueous Solution in Different "Culture Media"

For this purpose, PLL-F compounds are used. The evaluation is carried out by an "in-vitro" study that comprises:
- the observation of the appearance of the cells with the different "culture media"
- the cell counting for the monitoring of growth

APPLICATIONS

The complexes according to the invention can be used in numerous therapeutic or non-therapeutic applications.

For factor VIII, for example: today, if need be, the hemophiliac is to hydrate his freeze-dried solution, then prepare the proper dose, and finally inject himself. With the invention, the patient will just have to take the pre-filled syringe made available to him and inject the proper number of units. The higher the risk of under- or over-dosing, the higher the risk of contamination during preparation and thus overall safety for the patient.

In the field of diagnostics, the use of complexes according to the invention makes easier metering possible, and in nutraceutics, it makes it possible to put into solution a stable active ingredient in yogurt or the like, for example.

The invention claimed is:

1. Molecular complex that comprises:
   at least one polylysine (PLL) conjugate, comprising:
   a main PLL straight chain, and
   at least one molecule F that has a mean molecular weight of between 50 daltons and 1000 daltons and is linked covalently to said main chain, and
   at least one molecule M that is unstable in an ex-vivo storage solution with a hydrophilic and aqueous nature, said molecule M being an organic molecule or a protein with pharmacological and/or nutritional and/or cosmetic and/or diagnostic reagent activity,
   with the conjugate(s) and the molecule(s) M being linked by a non-covalent bond;
   wherein the complex comprising the non-covalently linked at least one PLL conjugate and the at least one molecule M are stable in the hydrophilic and aqueous ex-vivo storage solution;
   wherein stable and unstable in the hydrophilic and aqueous ex-vivo storage solution refers to:
   sufficiency to maintain the at least one molecule M in solution in the liquid phase, without it precipitating, and to
   sufficiency to maintain the molecule M's pharmacological and/or nutritional and/or cosmetic and/or diagnostic reagent activity,
   at a temperature that is higher than 0° C. for an entire period of storage up to several months; and
   wherein the molecular complex has the following characteristic:
   the molar ratio between the conjugate(s) and that of the molecule(s) M is between 1 and 30.

2. Molecular complex according to claim 1, wherein the molecule(s) F linked covalently to the main chain is (are) selected from among cysteine, methionine, taurine, glutathione, and thiotic acid.

3. Molecular complex according to claim 1, wherein the PLL comprises between 155 and 394 lysines.

4. Molecular complex according to claim 1, wherein the PLL of the conjugate is a straight alpha chain and/or wherein the molecular weight of each PLL is between 3000 daltons and 50000 daltons.

5. Composition that comprises at least one complex according to claim 1, in solution in a hydrophilic solvent.

6. Composition according to claim 5, further comprising at least one other compound in addition to the molecular complex and the hydrophilic solvent.

7. Method for obtaining a molecular complex according to claim 1, comprising the following steps:
   delivery of one or more PLL conjugates, comprising:
      a main PLL straight chain, and
      at least one molecule F that has a mean molecular weight of between 50 daltons and 1000 daltons and is linked covalently to said main chain, and
   delivery of one or more molecules M,
   bringing conjugate(s) into contact with the molecule(s) M under conditions that make it possible to form non-covalent bond(s) between the conjugate(s) and the molecule(s) M.

8. Method according to claim 7, further comprising at least one of the following characteristics:
   said step for ensuring contact is carried out at a temperature of between approximately 4° C. and 25° C. and in a buffered solution,
   the step for delivery of the conjugate(s) comprises the delivery of a solution that comprises the conjugate(s) in a hydrophilic solvent,
   said step for delivery of the molecule(s) M comprises the delivery of a solution that comprises the molecule(s) M in a hydrophilic solvent,
   the time period for bringing the conjugate(s) into contact with the molecule(s) M is between 1 hour and 24 hours.

9. Molecular complex according to claim 1, with the molecule M being an active pharmaceutical substance, for its use as a medication by itself or administered within a composition that comprises at least one complex according to claim 1, in solution in a hydrophilic solvent.

10. A method to improve the hydrophilic nature of a molecule M that is unstable in hydrophilic and aqueous ex-vivo storage solution, and/or to improve the stability in hydrophilic and aqueous ex-vivo storage solution of a molecule M that is unstable in hydrophilic and aqueous ex-vivo storage solution, and/or to improve in hydrophilic and aqueous ex-vivo storage solution the pharmacological and/or nutritional and/or cosmetic and/or diagnostic activity, of a molecule M that is unstable in hydrophilic and aqueous ex-vivo storage solution, comprising:
   providing at least one PLL conjugate, comprising:
      a main PLL straight chain, and
      at least one molecule F that has a mean molecular weight of between 50 daltons and 1000 daltons and is linked covalently to said main chain,
   in a hydrophilic solution; and
   forming a molecular complex according to claim 1.

* * * * *